(12) United States Patent
Jayaraman

(10) Patent No.: US 6,592,548 B2
(45) Date of Patent: *Jul. 15, 2003

(54) DELIVERY MECHANISM FOR BALLOONS, DRUGS, STENTS AND OTHER PHYSICAL/MECHANICAL AGENTS AND METHOD OF USE

(75) Inventor: Swaminathan Jayaraman, Fremont, CA (US)

(73) Assignee: Iowa-India Investments Company Limited of Douglas, British Isle (GB)

(*) Notice: Subject to any disclaimer, the term of this patent is extended or adjusted under 35 U.S.C. 154(b) by 0 days.

This patent is subject to a terminal disclaimer.

(21) Appl. No.: 09/760,846

(22) Filed: Jan. 17, 2001

(65) Prior Publication Data

US 2002/0010419 A1 Jan. 24, 2002

Related U.S. Application Data

(63) Continuation-in-part of application No. 09/305,138, filed on May 4, 1999, now Pat. No. 6,312,406, and a continuation-in-part of application No. 08/932,726, filed on Sep. 18, 1997, now Pat. No. 6,056,722.

(51) Int. Cl.$^7$ .............................................. A61M 29/00
(52) U.S. Cl. .............................. 604/103.04; 604/103.05
(58) Field of Search ...................... 604/102.01, 102.02, 604/103.04, 103.08, 160, 161, 523, 528, 103.05; 606/192, 194

(56) References Cited

U.S. PATENT DOCUMENTS

| 4,748,982 A | 6/1988 | Horzewski et al. |
| 4,762,129 A | 8/1988 | Bonzel |
| 5,077,311 A | 12/1991 | Karrer et al. |
| 5,170,286 A | 12/1992 | Zimmerberg et al. |
| 5,195,978 A | 3/1993 | Schiffer |
| 5,267,958 A | 12/1993 | Buchbinder et al. ... 604/103.05 |
| 5,334,147 A | 8/1994 | Johnson |
| 5,336,184 A | 8/1994 | Teirstein |
| 5,357,978 A | 10/1994 | Turk ........................... 604/913 |
| 5,380,283 A | 1/1995 | Johnson |
| 5,383,853 A | 1/1995 | Jung et al. |
| 5,387,226 A | 2/1995 | Miraki |
| 5,409,097 A | 4/1995 | Hoegger |
| 5,413,559 A | 5/1995 | Sirhan et al. |
| 5,413,560 A | 5/1995 | Solar |
| 5,443,456 A | 8/1995 | Alliger et al. |
| 5,443,457 A | 8/1995 | Ginn et al. |
| 5,458,613 A | 10/1995 | Gharibadeh et al. |
| 5,460,185 A | 10/1995 | Johnson et al. |
| 5,468,225 A | 11/1995 | Teirstein |
| 5,472,425 A | 12/1995 | Teirstein |
| 5,489,271 A | 2/1996 | Andersen |
| 5,501,227 A | 3/1996 | Yock |
| 5,507,731 A | 4/1996 | Hernandez et al. |
| 5,514,092 A | 5/1996 | Forman et al. |
| 5,531,690 A | 7/1996 | Solar |
| 5,545,134 A | 8/1996 | Hilaire et al. |

(List continued on next page.)

Primary Examiner—Anhtuan T. Nguyen
(74) Attorney, Agent, or Firm—Pennie & Edmonds LLP

(57) ABSTRACT

A balloon catheter for use with a guidewire is disclosed. The catheter has a body with a balloon located thereon, preferably at the distal end. A lumen within the catheter body communicates with the interior of the balloon which can be inflated by known methods with saline solution. A series of sleeve members of predetermined lengths and sizes are coupled to and positioned along the length of the catheter body. One or more of the sleeve members can span the length of the balloon. Each sleeve member has a passageway and both an exit and entry port so that the guidewire can pass therethrough. Instead of a balloon, the catheter can include a device member that forms a chamber which can store medicine until discharged at the desired site within the blood vessel. Apertures or pores on the catheter body allow for the perfusion of blood or the delivery of medicine to the site of the blood vessel. A method of operation is also disclosed.

29 Claims, 11 Drawing Sheets

U.S. PATENT DOCUMENTS

| | | |
|---|---|---|
| 5,549,553 A | 8/1996 | Ressemann et al. |
| 5,549,556 A | 8/1996 | Ndondo-Lay et al. |
| 5,578,009 A | 11/1996 | Kraus et al. |
| 5,598,844 A | 2/1997 | Diaz et al. |
| 5,607,394 A | 3/1997 | Andersen et al. ...... 604/102.01 |
| 5,607,406 A | 3/1997 | Hernandez et al. ......... 604/264 |
| 5,620,417 A | 4/1997 | Jang et al. ............. 604/103.04 |
| 5,626,600 A | 5/1997 | Horzewski et al. ......... 606/194 |
| 5,645,533 A | 7/1997 | Blaeser et al. ......... 604/164.01 |
| 5,752,932 A | 5/1998 | Ellis et al. ................ 604/96.01 |
| 6,056,722 A * | 5/2000 | Jayaraman ............. 604/102.01 |
| 6,312,406 B1 * | 11/2001 | Jayaraman ............. 604/103.04 |

\* cited by examiner

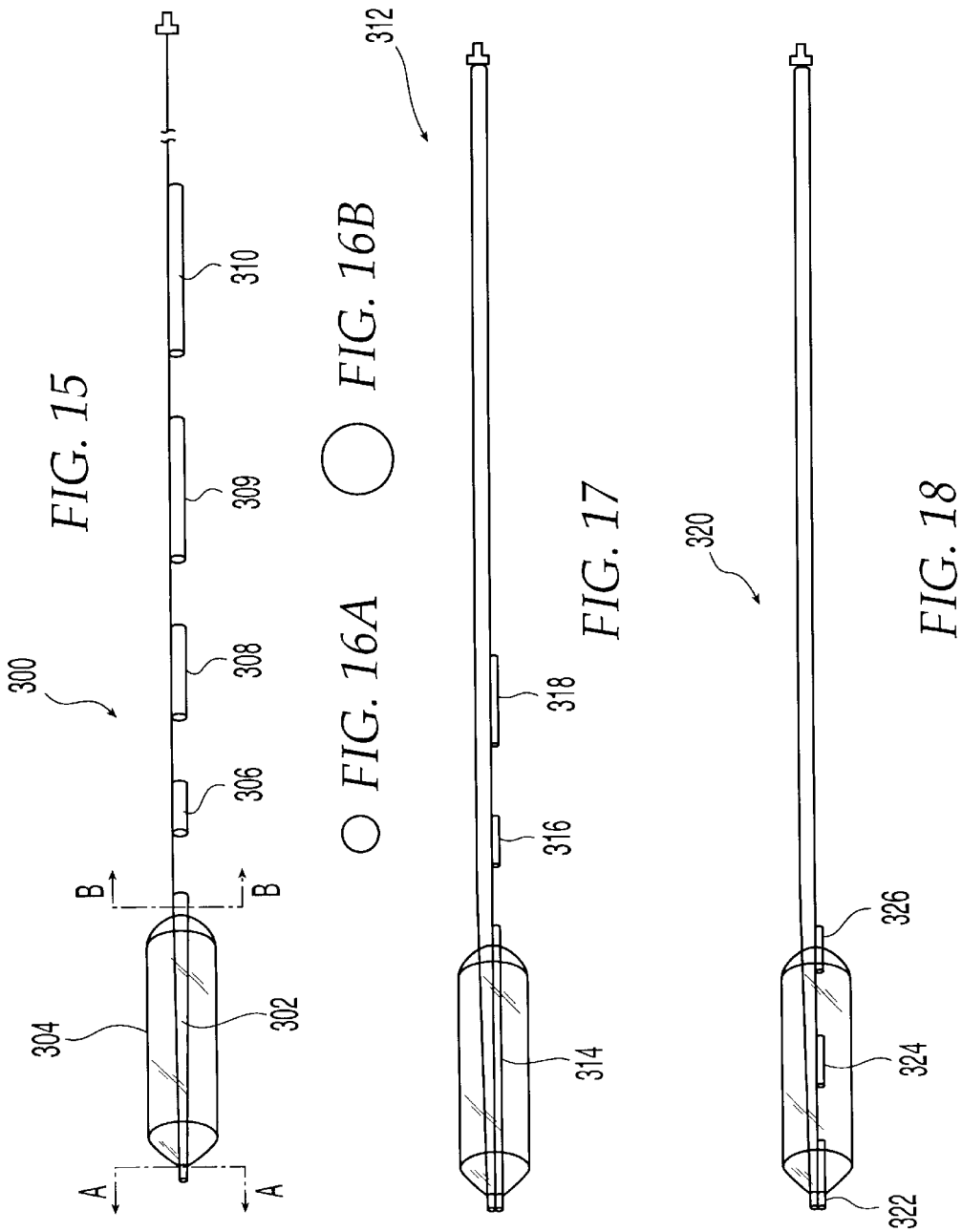

DELIVERY MECHANISM FOR BALLOONS, DRUGS, STENTS AND OTHER PHYSICAL/MECHANICAL AGENTS AND METHOD OF USE

CROSS-REFERENCE TO RELATED APPLICATIONS

This application is a continuation-in-part of prior patent application Ser. No. 09/305,138, filed May 4, 1999, now U.S. Pat. No. 6,312,406, and is a continuation-in-part of prior patent application Ser. No. 08/932,726, filed Sep. 18, 1997, now U.S. Pat. No. 6,056,722. The entire content of both these applications is expressly incorporated herein by reference thereto.

FIELD OF THE INVENTION

The present invention is directed to catheters for delivering balloons, drugs, stents, and other devices or agents into the arterial or venal systems of the human body. In particular, this invention relates to catheters that provide a quick, efficient, and rapid exchange capability for the delivery of an angioplasty balloon into the arterial vessels of the human heart.

BACKGROUND ART

The human body includes arterial and venous conduits which run throughout various sections of the human body. These conduits conduct blood into and from the heart which maintain the circulation that helps to sustain the metabolic events in the body. The vessels undergo biological, physiological, and mechanical changes depending on the body metabolism which determine the functionality of the wall of the artery.

Sometimes the wall of an artery becomes occluded due to deposits of fatty tissues which in turn form plaque on the walls of the artery. These plaques then have to removed to restore the normal function of the artery. One known mechanism of removing the plaque is to compress the plaque against the wall of the artery using a balloon catheter. This procedure is called Per cutaneous (under the skin) Transluminal (under x-ray guidance) Coronary (region of intervention) Angioplasty (plaque compression) or PTCA.

For a PTCA procedure to be accomplished, a balloon catheter and a guidewire along with a guiding catheter are typically required. The guiding catheter is normally introduced in a groin artery and pushed upwards towards the aorta until it reaches the mouth of the coronary artery. Once the guiding catheter is placed at the opening of the coronary artery, a highly floppy wire is introduced into the guiding catheter such that the wire crosses the mouth of the guiding catheter and goes into the coronary artery. It then has to reach the site of the lesion (plaque) which is usually a very tortuous route and the operator (the cardiologist) has to struggle to reach the guidewire in place. Once a guidewire has crossed the lesion, it is then pushed distally to the lesion so that it remains at a safe place. This is to ensure that the wire does not slip out of the lesion.

A catheter which has a balloon at one end and a shaft at the other end is usually introduced into the lesion on top of the guidewire. Although the mechanism of introduction and the design of the catheter that facilitate the mechanism have been improved by known catheters, they still leave room for improvement.

Several designs of balloon catheters are disclosed in various U.S. patents that facilitate insertion into the artery using a guidewire as an intermediate tool. The way in which the balloon travels on top of the guidewire and the length of the catheter that travels on top of the guidewire is the subject of known devices such as those shown and described in U.S. Pat. Nos. 5,620,417; 5,607,406; 5,607,394; 5,598,844; 5,549,556; 5,545,134; 5,531,690; 5,514,092; 5,077,311; 5,501,227; 5,489,271; 5,472,425; 5,468,225; 5,460,185; 5,458,613; 5,443,457; 5,413,560; 5,413,559; 5,409,097; 5,387,226; 5,383,853; 5,380,283; 5,357,978; 5,336,184; 5,334,147; 5,195,978; 5,170,286; 4,748,982; 4,762,129; and 5,626,600, all of which are incorporated herein in their entirety.

While each one of these above-listed patents describe and illustrate several ways of approaching the traverse mechanism, all of them essentially assume the following: (1) the catheter has proximal and distal ends; (2) there is a balloon mounted on the distal end; (3) the proximal end has a shaft; (4) the interior of the balloon is in communication with a lumen; (5) there is another sleeve that either extends towards the entire length of the catheter or runs at a fixed distance from the distal end of the catheter; (6) the sleeve, if it does not run the entire length of the catheter, extends up to a predetermined distance from the balloon up to the midsection of ⅓ of the entire catheter length or sometimes shorter; (7) the portion of the sleeve is called the flexible portion, while the proximal portion is either a hollow tube or an elliptical structure which provides for pushability of the catheter; (8) the sleeve has one opening at the proximal side of the balloon through which a guidewire can be inserted and it comes out through the center of the balloon—this is commercially known as the rapid exchange or the monorail concept; and (9) in instances in which the sleeve extends along the entire length of the balloon, the wire extends inside the sleeve from the distal to the proximal end of the catheter through the balloon—this is called the over the wire concept.

In the devices of the above patents, regardless of whether the catheter is over the wire or monorail, the guidewire has one entry point and one exit point and the regions between the entry and exit are imbedded in the catheter sleeve or the catheter shaft.

However, the catheters of the above patents have some serious disadvantages in lesions that are completely occluded or in lesions that have severe tortuosity. In lesions that have complex distal diseases the catheter has to traverse multiple bifurcations in order to reach the site of lesion. In case of the above described known catheters, the operator or the cardiologist forces the body of the catheter on top of the wire using an external force. This force then transmits from the catheter body to the surface of the wire. When the wire is held with a counteractive force, the force against the catheter becomes greater and a law of physics comes into play, the object with the greatest force moves forward.

In balloon angioplasty, it is desired to design a catheter which pushes on top of a wire with a minimum force. In order to achieve this, catheters with very low profiles are sought. These low profiles enable easy slippage on top of the wire. Sometimes the wires are also coated with a lubricous coating to enable ease of passage of the catheter.

In numerous instances, the operator is unable to cross a lesion with a rapid exchange catheter. He then switches over to an over the wire design or vice versa when the operator cannot transmit the necessary force for the balloon catheter to traverse the lesion.

In general rapid exchange catheter designs are preferred because there is only about ⅓ of the catheter body that is imbedded in the guidewire and hence the force required for the catheter to travel is less. In the case of total occlusions, over the wire designs are preferred as the catheter. If the catheter is being pushed through a very hard plaque or a totally occluded artery, the maximum force from the proximal end of the catheter has been delivered to the distal end.

The force delivered at the proximal end by the operator relates to the force of balloon moving forward toward the lesion. There are forces lost between the proximal end to the distal end of the catheter and this happens due to the tortuosity of the lesions, length of the shaft of the catheter and also lesion morphology.

Prior art inventions are easily understood if we draw a very simple analogy between the catheter and the guidewire. Assume the guidewire is the track of the train, and the catheter is the train. In the rapid exchange design, the train has one pair of small wheels that are the distal ⅓ of the catheter of the length of the sleeve. In the case of an over the wire design, the train has one pair of long wheels from the distal end of the catheter to the proximal end.

SUMMARY OF THE INVENTION

The present invention is directed to a catheter comprising body member having a lumen; balloon member disposed on the body member and communicating with the lumen; and plurality of sleeve members disposed on the body member, each sleeve member having a passageway therethrough.

In one preferred embodiment, at least one of the sleeve members is disposed in a distal region of the elongated member. The at least one of the sleeve members can be disposed adjacent the balloon member and can have a length less than that of the balloon member. The at least one of the sleeve members can be disposed within the balloon member.

According to a catheter of the present invention, at least one of the sleeve members can be disposed adjacent the balloon member and have a length greater than that of the balloon member. The at least one of the sleeve members extends through the balloon member.

In another preferred embodiment, the at least one of the sleeve members can be disposed generally centrally of the balloon member.

In alternative embodiments, the at least one of the members can be disposed generally eccentrically of the balloon member, or generally outside of the balloon member, or proximally of the balloon member. The remaining sleeve members can be equally sized and equally spaced along the catheter body. Alternatively, the remaining sleeve members can be differently sized and differently spaced along the catheter body. Preferably there are two or three remaining sleeve members.

The present invention is also directed to an angioplasty catheter comprising elongated body member having a lumen which includes an opening adjacent its distal end and at least one opening adjacent its proximal end; balloon member sealingly disposed on the elongated member adjacent its distal end, the elongated member having at least one opening communicating with the interior of the balloon and the lumen within the elongated body member; and plurality of sleeve members disposed on the elongated member, each sleeve member having a passageway therethrough.

An angioplasty catheter, according to the present invention, can also comprise guidewire dimensioned and configured for passing through the passageway of the sleeve members.

The present invention is also directed to a catheter comprising body member having a lumen; and plurality of sleeve members disposed on the body member, each sleeve member having a passageway therethrough.

A catheter, according to the present invention, comprises generally rigid body member having a lumen; balloon member disposed on the body member and communicating with said lumen; and plurality of generally flexible sleeve members disposed on the body member, each sleeve member having a passageway therethrough.

The present invention also is directed to a catheter which comprises body member having a lumen; device member disposed on the body member; and plurality of sleeve members disposed on the body member, each sleeve member having a passageway therethrough. The device member can be a stent or a container having a chamber for containing a drug.

Also, the present invention is directed to a method of using a catheter comprising providing a catheter including body member having a lumen; balloon member disposed on the body member and communicating with the lumen; and plurality of sleeve members disposed on the body member, each sleeve member having a passageway therethrough; selectively passing a guidewire through the passageways of the sleeve members, the guidewire being disposed in a body cavity, so as to position the catheter at a desired location within the body cavity; and selectively inflating the balloon and withdrawing the catheter from within the body cavity.

The present invention is also directed to a method of using a catheter comprising providing a catheter including body member having a lumen; device member disposed on the body member; and plurality of sleeve members disposed on the body member, each sleeve member having a passageway therethrough; selectively passing a guidewire through the passageways of the sleeve members, the guidewire being disposed in a body cavity, so as to position the catheter at a desired location within the body cavity; and selectively operating the device member within the body cavity.

According to one preferred embodiment wherein the device member comprises a container having a chamber containing a drug, the method further comprises releasing the drug from the chamber. Alternatively, wherein the device member comprises a stent, the method further comprises releasing the stent within the body cavity.

The present invention is also directed to a catheter comprising body member having a lumen; balloon member disposed on said body member and communicating with the lumen; and plurality of sleeve members disposed on the body member, each sleeve member having a passageway therethrough, at least one or more sleeve members disposed adjacent the balloon member and along at least a portion of the length of the balloon member, and wherein the balloon adjacent sleeve members have a generally non uniform cross-section. In a preferred embodiment, at least one of said balloon adjacent sleeve members is generally conical and has a cross-section generally increasing in the proximal direction. Also, at least one of the sleeve members is disposed in a distal region of said elongated member. In addition, at least one of the sleeve members is disposed adjacent the balloon member and has a length less than that of the balloon member. Furthermore, at least one of the sleeve members can be disposed within the balloon member. At least one of the sleeve members is disposed adjacent the balloon member and has a length greater than that of the balloon member. At least one of the sleeve members extends through the balloon member.

At least one of the sleeve members can be disposed in one of following configurations, i.e., generally centrally, eccentrically, generally outside, or proximally of the balloon member. The remaining sleeve members can be equally sized and equally spaced along the catheter body. Also they can be differently sized and differently spaced along the catheter body. In preferred embodiments, there are two or three remaining sleeve members. The body member can have a plurality of apertures on said body member.

Also the present invention can be directed to an angioplasty catheter comprising elongated body member having a lumen and having an opening at its proximal end and at least one opening adjacent its distal end; elongated balloon member sealingly disposed on the elongated body member adjacent its distal end, the elongated body member having at least one opening communicating with the interior of the balloon and the lumen within the elongated body member; plurality of sleeve members disposed on the elongated member, each sleeve member having a passageway therethrough, at least one or more sleeve members disposed adjacent the balloon member and along at least a portion of the length of the balloon member, and wherein the balloon adjacent sleeve members have a generally non uniform cross-section; and guidewire dimensioned and configured for passing through the passageway of the sleeve members.

Method of using a catheter comprises providing a catheter comprising: body member having a lumen; balloon member disposed on the body member and communicating with the lumen; and plurality of sleeve members disposed on the body member, each sleeve member having a passageway therethrough, at least one or more sleeve members disposed adjacent the balloon member and along at least a portion of the length of the balloon member, and wherein the balloon adjacent sleeve members have a generally non uniform cross-section; selectively passing a guidewire through the passageways of the sleeve members, the guidewire being disposed in a body cavity, so as to position the catheter at a desired location within the body cavity; and selectively inflating the balloon. At least one of the balloon adjacent sleeve members is generally conical and is provided with a cross-section that is generally increasing in the proximal direction.

The present invention is also directed to a catheter in which a peelable sheath covers the sleeve members to facilitate the insertion of a guidewire through the passageways of each of the sleeve members. The present invention also relates to a method of using such a catheter. With a portion of a guidewire extending out of the patient, the guidewire is introduced into the entry port of the distal-most sleeve member. Because the sheath covers the other ports of the sleeve members, inserting the guidewire through the passageways of the other sleeve members does not requiring threading through the entry and exit ports. The sheath is then peeled away and the catheter can be inserted in the patient along the guidewire.

BRIEF DESCRIPTION OF THE DRAWINGS

The present invention is described in detail below with reference to the drawings wherein:

FIG. 15 is a side view of a different embodiment of a balloon catheter according to the present invention wherein the guidewire channel inside the balloon has a different diameter along the length of the channel.

FIGS. 16A and 16B are a cross-sectional view of the catheter of FIG. 15 taken along the lines A—A and B—B, respectively, to illustrate the larger diameter at the proximal end portion of the guidewire lumen inside the balloon.

FIG. 17 is a side view of still another embodiment of a balloon catheter according to the present invention wherein the guidewire channel is parallel to the body member inside the balloon and wherein the sleeves are of varying length and spaced equidistantly.

FIG. 18 is a side view of still another embodiment of a balloon catheter according to the present invention wherein the guidewire channel is parallel to the body member inside the balloon and includes three sleeve members.

DETAILED DESCRIPTION OF THE PREFERRED EMBODIMENTS

In the description which follows, any reference to direction or orientation is intended primarily and solely for purposes of illustration and is not intended in any way as a limitation to the scope of the present invention. Also, the particular embodiments described herein, although being preferred, are not to be considered as limiting of the present invention.

An invention is hereby described which applies the laws of physics and also the general principle of train on a track. A train moves on a track with multiple wheels which are positioned at equal distances form the engine. The present invention applies this principle to a catheter by having multiple entry points and exit points of a catheter body for the passage of a guidewire.

From physics it is known that the force required to push an object on top of another depends on the surface area of coverage and the nature of the radial coverage that enables a longitudinal force to be transmitted while the object is being pushed on top of the other object.

Figure 1A:
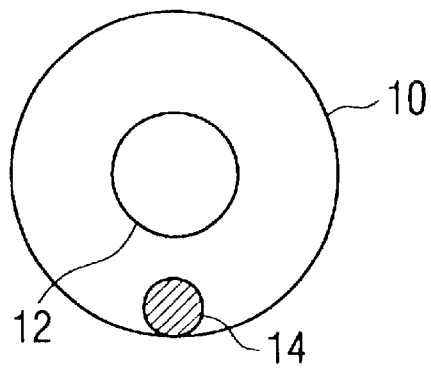
FIG. 1A is a cross-sectional view of a balloon catheter according to the prior art taken along the midsection of the balloon, wherein the balloon lumen is in the center and the guidewire lumen is eccentric to the balloon but in the shaft of the catheter.
Figure 1B:
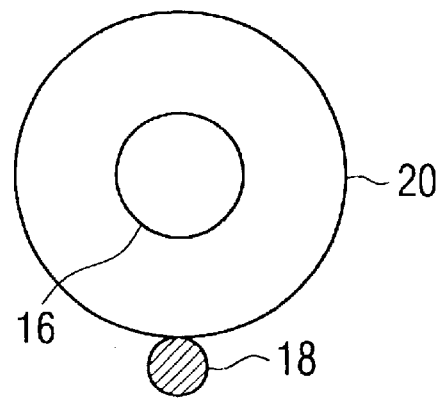
FIG. 1B is a cross-sectional view of a balloon catheter according to the prior art wherein the balloon lumen is in the center and the guidewire lumen is eccentric to the shaft.
Figure 1C:
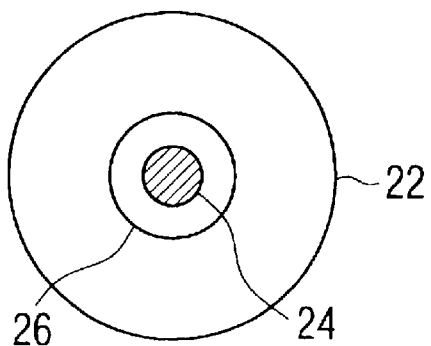
FIG. 1C is a cross-sectional view of a bi-lumen catheter according to the prior art wherein the guidewire lumen and the balloon lumen are concentric to the shaft of the catheter.
Figure 1D:
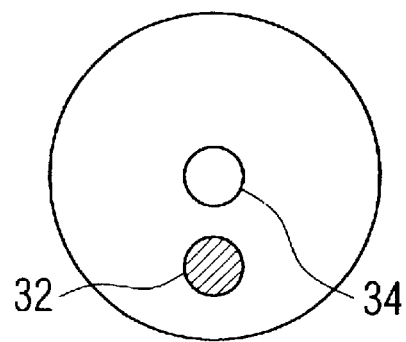
FIG. 1D is a cross-sectional view of the balloon catheter according to the prior art wherein the guidewire lumen and the balloon lumen are in a symmetrical axis to each other.

Various known balloon catheter configurations are shown in FIGS. 1A–1D and FIGS. 2A–2D. In FIG. 1A, a balloon 10 is shown with an internally and centrally positioned balloon lumen 12 and a guidewire lumen 14 which is in the shaft of the catheter but eccentric to the balloon 10. In the catheter shown in FIG. 1B, the balloon lumen 16 is centrally located within the balloon 20 and the guidewire lumen 18 which is eccentric to the shaft and the balloon 20. The catheter shown in FIG. 1C has a balloon 22 with internal guidewire lumen 24 and surrounding balloon lumen 26. Both guidewire lumen 24 and balloon lumen 26 are concentric to the shaft of the catheter. In FIG. 1D, the guidewire lumen 30 and balloon lumen 34 are positioned within balloon 36 so that the balloon lumen 34 is centrally positioned and the guidewire lumen 30 is outside of the balloon lumen 34.

Figure 2A:
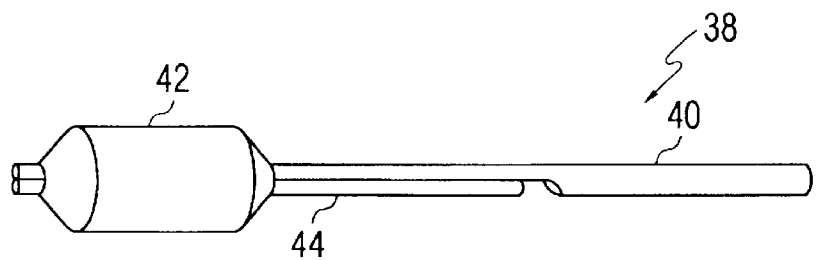
FIG. 2A is a side view of a balloon catheter according to the prior art wherein the guidewire sleeve exits proximally out of the balloon about ⅔ the length of the catheter.
Figure 2B:
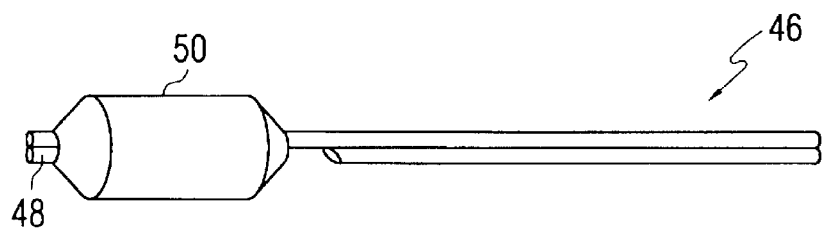
FIG. 2B is a side view of a balloon catheter according to the prior art wherein the guidewire sleeve exits at the proximal tip of the balloon.
Figure 2C:
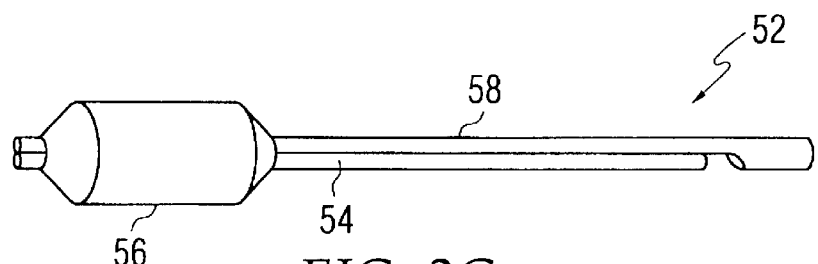
FIG. 2C is a side view of a balloon catheter according to the prior art wherein the guidewire sleeve exits adjacent but prior to the proximal end of the catheter.
Figure 2D:
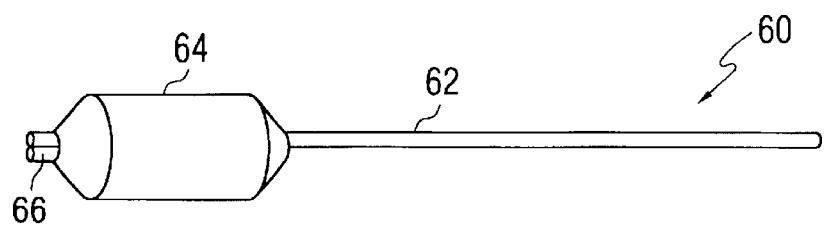
FIG. 2D is a side view of another embodiment of a balloon catheter according to the prior art wherein the guidewire sleeve exits at the proximal end of the catheter.

In reference to FIG. 2A, a known catheter 38 includes a catheter body 40 with a distally positioned balloon 42. A guidewire lumen 44 for a guidewire (not shown) extends from the distal end of the catheter but exits before the full length of the catheter 38. In the catheter 46 of FIG. 2B, the guidewire lumen 48 extends through the balloon 50 and exits at the proximal end of the balloon 50. In another known catheter 52 shown in FIG. 2C, the guidewire lumen 54 extends through the balloon 56 and extends closely to the proximal end of the catheter body 58. As shown in FIG. 2D, the catheter 60 has a catheter body 62, a balloon 64 and a guidewire lumen that extends the length of the balloon 64.

Figure 3A:
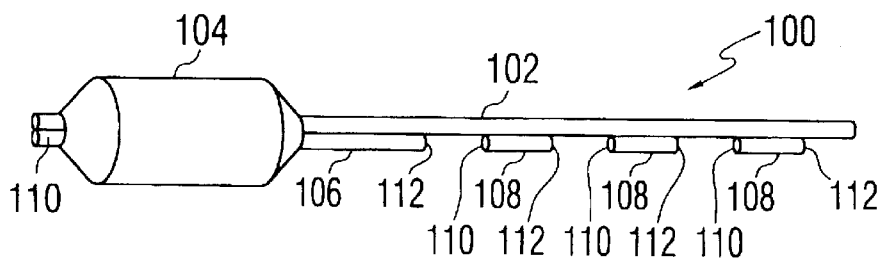
FIG. 3A is a side view of an embodiment of a balloon catheter according to the present invention wherein the guidewire sleeve is formed of four spaced apart sleeve members and wherein the sleeve member through the balloon is the longest.

Referring to FIG. 3A, a balloon catheter 100 according to the present invention has a catheter body 102 and a distal balloon 104. Coupled to the catheter body 102 are four sleeve members including the longest member 106 that spans the balloon 104. The other three sleeve members 108 are equal in size and spaced apart from each other and sleeve member 106. Each sleeve member 106 and 108 has an entry port 110 which is located at the most distal end of the sleeve member and an exit port 112 located at the proximal end of the respective sleeve member. Thus the sleeve members provide multiple points of entry for the guidewire (not shown) and corresponding multiple points of exit for the guidewire. The exit port 112 for the largest sleeve member 106 is proximal to the proximal end of the balloon 104 either concentric or eccentric to the balloon 104. Alternatively, the other ports of exit 112 can be located at various distances along the length of the catheter 100. These ports of entry and exit can be located at various predetermined locations. Various desired predetermined configurations of displacements of the sleeve members 106 and 108 can be utilized as well as various lengths of the different sleeves. These points run along the entire length of the catheter or can run only in the distal part of the catheter.

Depending on the lesion morphology and also the tortuosity of the lesion, the length of the catheter which runs on the guidewire can be selected.

In one preferred embodiment, a catheter can have four points, five or up to ten points of entry and five, six or up to 10 points of exit. In an alternative embodiment, the catheter can have seven to nine points of entry and seven to nine points of exit.

Depending on the length of the coverage of each, the exposed segments of the catheter between the sleeve members act as wheels. Hence the catheter of the present invention provides multiple wheels that guide the catheter.

The first point of entry is ideally located at the tip of the balloon and can run concentric to the balloon axis or can run eccentric to the balloon axis, the first point of exit is located just after the balloon or a short distance proximal to it. The second point of entry is located at a distance greater than the first point of entry and subsequent exit at second pint. The distance between the first point of exit and the second point of entry is the exposed part of the wire in the body of the catheter. This exposed part of the wire is called the "wire segment". The distance between the second point of entry and the second point of exit is called the "catheter segment", the wire segment and the catheter segment can alternate along the entire length of the catheter or only on the distal ⅓ of the catheter.

A catheter is also described wherein the first point of entry is located distal to the location of the balloon such that the wire does not pass inside the lumen of the balloon. In such a case the catheter shaft that has "wire segments" and "catheter segments" is taken at the site of the lesion, the wire pulled back such that it is proximal to the balloon and the balloon is then dilated at the site of the lesion.

Figure 3B:
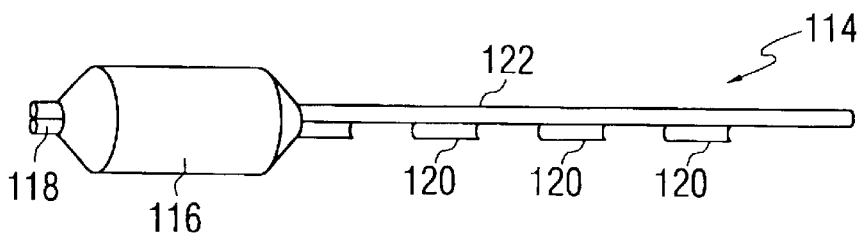
FIG. 3B is a side view of another embodiment of a balloon catheter according to the present invention wherein the guidewire sleeve is formed of four spaced apart sleeve members and wherein the guidewire lumen is eccentric to the balloon lumen and exits proximal to the balloon.
Figure 3C:
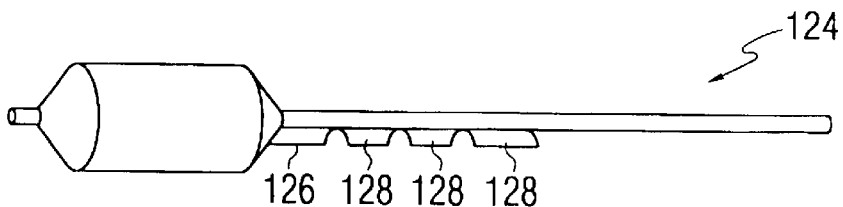
FIG. 3C is a side view of an yet another embodiment of a balloon catheter according to the present invention wherein the guidewire sleeve is formed of four spaced apart sleeve members which are more closely spaced than the sleeve members in FIG. 3A or 3B.

Referring to FIG. 3B, the catheter 114, similar to that shown in FIG. 3B, has a balloon 116 and four sleeve members 118 and 120 which are equally spaced apart. Sleeve member 118 is the longest and spans the balloon 116. Unlike catheter 100 wherein sleeve member 106 is a separate tubular structure coupled to catheter body 102, sleeve member 118 in catheter 114 can be formed as part of the catheter body 122. In the alternative embodiment of FIG. 3C, the catheter 124 has four sleeve members 126 and 128 that are more closely spaced than in FIGS. 3B and 3C.

Figure 3D:
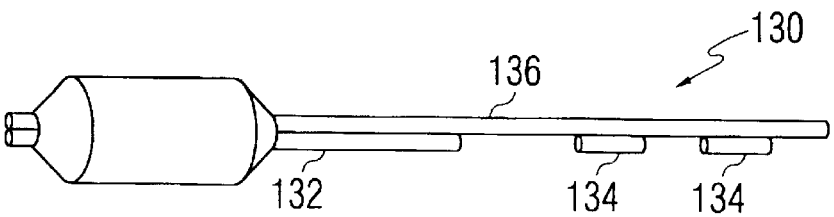
FIG. 3D is a side view of an still another embodiment of a balloon catheter according to the present invention wherein the guidewire sleeve is formed of three spaced apart sleeve members and wherein the sleeve member through the balloon is the longest.
Figure 3E:
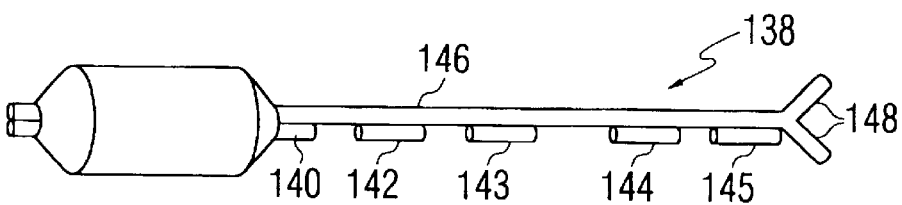
FIG. 3E is a side view of an still yet another embodiment of a balloon catheter according to the present invention wherein the guidewire sleeve is formed of five different sized and differently spaced apart guidewire sleeve members.

In yet another alternative embodiment, catheter 130 in FIG. 3D includes three sleeve member 132 and 134 which are spaced at different intervals along the catheter body 136. Still another embodiment 138 shown in FIG. 3E has five different spaced and different sized sleeve members 140, 142, 143, 144, and 145. The catheter 138 has a catheter body 146 that at its proximal end has a Y-lumen configuration 148.

Figure 4A:
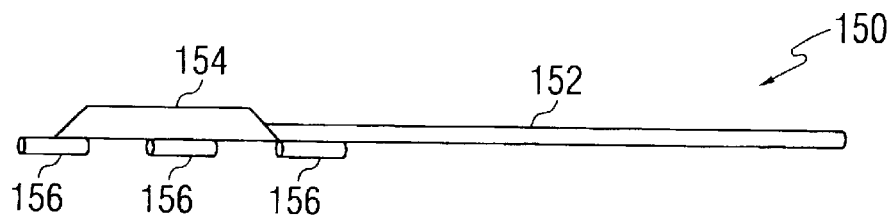
FIG. 4A is a side view of an embodiment of a balloon catheter according to the present invention wherein the guidewire sleeve is formed of three spaced apart sleeve lumens located along and extending beyond the ends of the balloon and wherein the guidewire lumen is eccentric to the balloon.
Figure 4B:
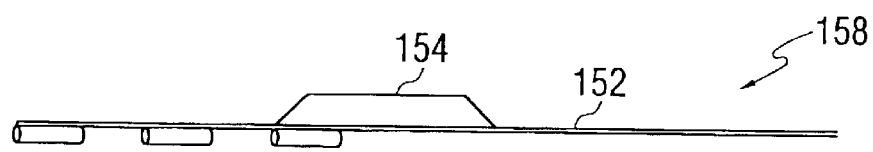
FIG. 4B is a side view of an embodiment of a balloon catheter according to the present invention wherein the guidewire sleeve is formed of three spaced apart sleeve lumens and wherein two sleeve lumens are positioned distally of the balloon and the remaining sleeve lumen is positioned in the region of the balloon and wherein the guidewire lumen is eccentric to the balloon.
Figure 4C:
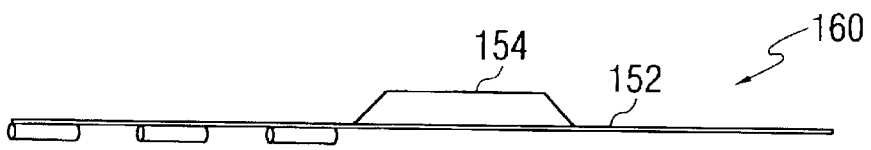
FIG. 4C is a side view of an yet another embodiment of a balloon catheter according to the present invention wherein the guidewire sleeve is formed of three spaced apart sleeve lumens positioned distally of the balloon and wherein the guidewire lumen is eccentric to the balloon.
Figure 4D:
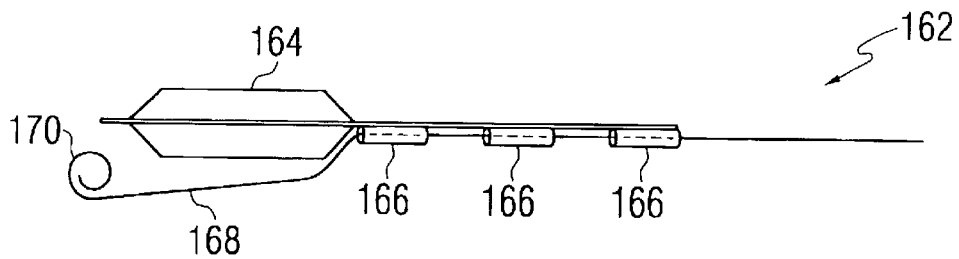
FIG. 4D is a side view of still yet another embodiment of a balloon catheter according to the present invention wherein the guidewire sleeve is formed of three spaced apart sleeve lumens positioned proximally of the balloon.

Turning to the catheter embodiment 150 shown in FIG. 4A, a catheter body 152 has a balloon structure 154 (shown schematically) at the distal end of the catheter 150. Three equally sized and spaced sleeve members 156 are positioned distally and span the length of the half balloon 154. In the alternative embodiments 158 and 160 illustrated schematically in FIGS. 4B and 4C, the balloon 154 is located on the catheter body 152 closer to the proximal end of the catheters 158 and 160. In the embodiment 162 of FIG. 4D, the balloon 164 is positioned distally of the sleeve members 166 that receive guidewire 168 that passes through the passageways of each sleeve member 166. In the exemplary embodiment of FIG. 4D, the guidewire 168 has a curled distal end 170 but straight configurations can also be employed with the catheters of the present invention.

Figure 6:
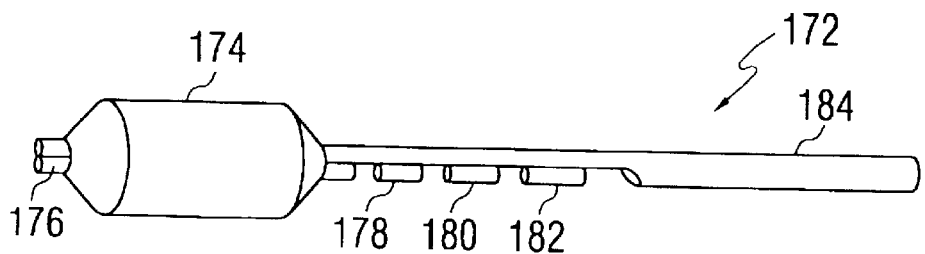
FIG. 6 is a side view of an embodiment of a balloon catheter according to the present invention wherein the guidewire sleeve is formed of four spaced apart sleeve members and wherein the sleeve member through the balloon is the longest.
Figure 7:
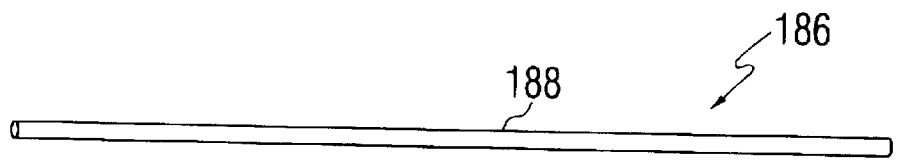
FIG. 7 is a side view of a generally rigid tube for use with the balloon catheter of FIG. 8.
Figure 8:
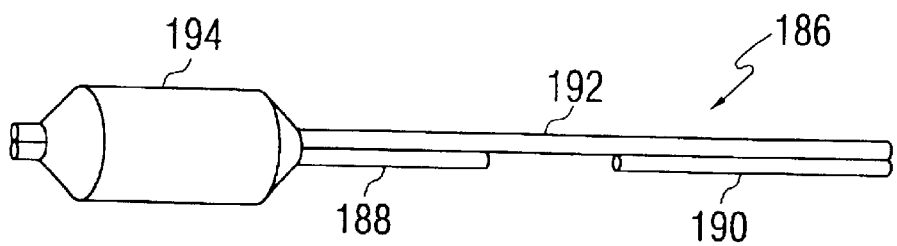
FIG. 8 is a side view of an yet another embodiment of a balloon catheter according to the present invention wherein the guidewire sleeve is formed of two spaced apart sleeve members and wherein the balloon is disposed on a flexible sheath which is coupled to the generally rigid tube of FIG. 7 so that the flexible portion is distal and the rigid portion is proximal.

Referring to FIG. 6, a catheter 172 includes a 174 and four sleeve members 176, 178, 180, and 182 which are coupled to a shaft 184 that has a larger diameter proximal end portion. FIGS. 7 and 8 illustrate two parts of balloon catheter 186 that can be combined to form the catheter. The structure of FIG. 7 is a generally rigid tube 188. In FIG. 8, the guidewire sleeve is formed of two separate members 188 and 190 that are connected to a balloon lumen 192 that allows for inflation of balloon 194. The balloon lumen 192 is a generally flexible sheath which can be coupled to the generally rigid tube shown in FIG. 7. After combining the components of catheter 186, the flexible portion is distal and the rigid portion is proximal.

Figure 9:
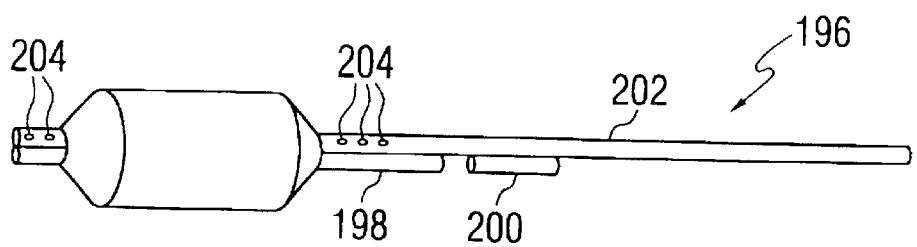
FIG. 9 is a side view of an still another embodiment of a balloon catheter according to the present invention wherein the guidewire sleeve is formed of two spaced apart sleeve members and the catheter shaft includes proximal and distal apertures for perfusion of blood during angioplasty.

In the embodiment of FIG. 9, the balloon catheter 196 has a guidewire sleeve that is formed of two spaced apart sleeve members 198 and 200. Included on the catheter shaft 202 are proximal and distal apertures 204 that allow for the perfusion of blood during angioplasty. In the catheter 206 shown in FIG. 10, microporous holes 208 are provided along the length of the catheter shaft 210. Guidewire lumens (not shown) according the present invention can be attached to the shaft 210 at various locations along the catheter body.

In general, each sleeve member of the various embodiments disclosed and described herein has an entry port 110 and an exit port 112 as shown and discussed in connection with the catheter 100 of FIG. 3A. Also, each sleeve member has a passageway to accommodate the passage of the guidewire. The embodiments herein demonstrate that various sized and spaced sleeve members can be employed to allow for passage of a guidewire. Also, the guidewire lumens can be attached or coupled to the catheter shaft by various known methods of attachment. Alternatively, the guidewire lumens can be formed integrally with the catheter body.

The invention also covers other interventional devices apart from the balloon to include stents, mounted on balloons or otherwise, drug delivery devices where the media can be delivered distal to the balloon or proximal to the balloon. Thus the catheter of the present invention allows for improved pushability and control over that available with known catheters. The balloon can be made of compliant, semi-compliant or a non-compliant polymeric material, or a combination of a polymeric material. Additionally, the exterior surface of the balloon can be coated with an antibiotic or other pharmacological agent(s) so that the agent(s) are applied to the lesion when the balloon is expanded. The body member can be made of metal, plastic or a combination of both. The sleeve member is preferably made of plastic, polymeric material. In use, the balloon can be inflated with saline or a contrast fluid as is known by those skilled in the art.

Figure 10A:
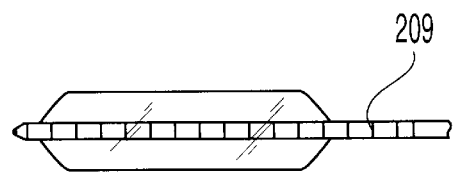
FIG. 10A is a side view of another embodiment of a balloon catheter according to the present invention wherein the catheter has radiopaque markers to provide indicia.
Figure 10:
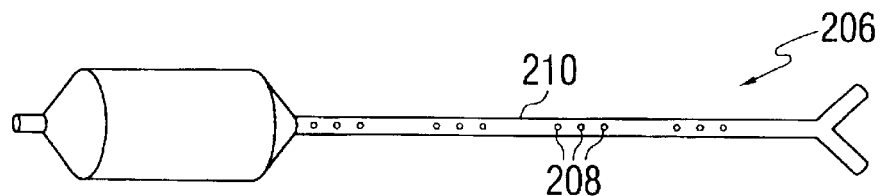
FIG. 10 is a side view of an still yet another embodiment of a balloon catheter according to the present invention wherein the catheter shaft has microporous holes disposed along the shaft for drug delivery.

As shown in FIG. 10A, radiopaque markers 209 can be place on the balloon, body member, and/or sleeve members to determine positioning of the catheter. Markers 209 allow the length of the lesion to be measured, both before, during, and after inflation of the balloon. Such measurement can be helpful, for example, in selecting the appropriate size of a stent. Markers 209 can be made of any radiopaque material, such as gold or a radiopaque ink, which will not increase the profile of the catheter.

Figure 11:
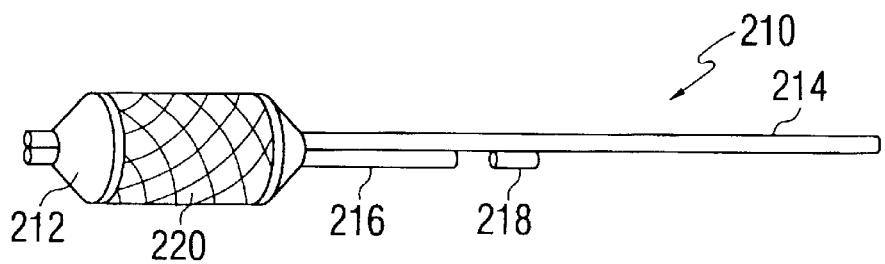
FIG. 11 is a side view of an yet another embodiment of a balloon catheter according to the present invention wherein the guidewire sleeve is formed of two spaced apart sleeve lumens and wherein the balloon carries a stent.
Figure 12:
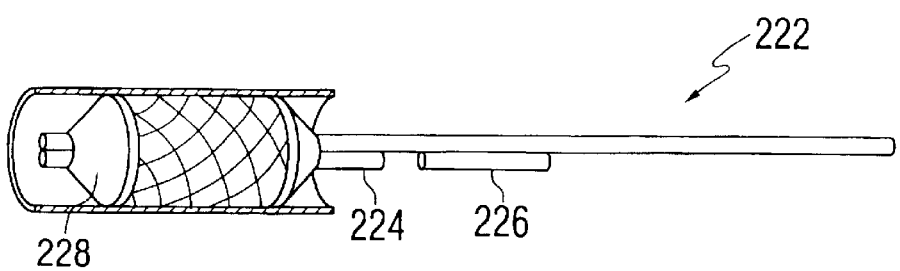
FIG. 12 is a side view of the balloon catheter of FIG. 11 having different sized sleeve members and further including a sheath on the stent for removal and inflation.
Figure 13:
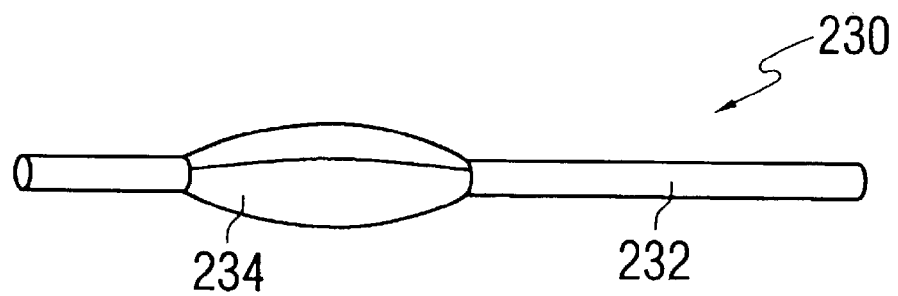
FIG. 13 is a side view of a drug delivery catheter in a closed configuration.
Figure 14:
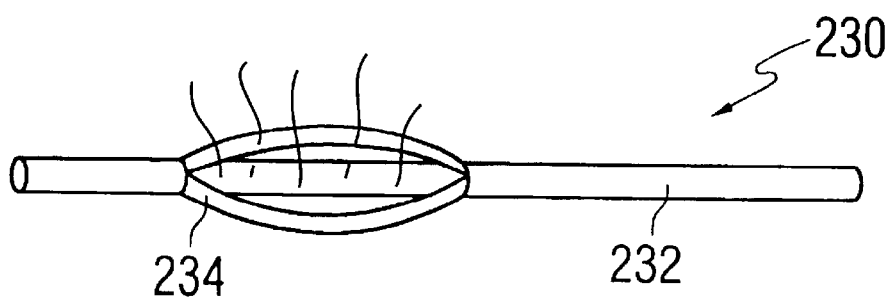
FIG. 14 is a side view of the drug delivery catheter of FIG. 13 in an open configuration.

In the embodiment illustrated in FIG. 11, a balloon catheter 210 includes a balloon 212 disposed on a catheter shaft or balloon lumen 214 which has guidewire lumens 216 and 218. A stent 220 is positioned on and carried by the balloon 212. After the balloon 212 is located at the preferred or desired site within a blood vessel, the stent can be released, the balloon deflated and the catheter 210 removed. In the embodiment shown in FIG. 12, the catheter 222 also includes a sheath on the stent for removal and inflation. Different sized and positioned guidewire lumens 224 and 226 can be used with balloon 228. Drug delivery catheters 230 are shown in FIGS. 13 and 14 which can be used with the guidewire lumens (not shown) of the present invention. In FIG. 13, the catheter 230 is shown as including a catheter shaft 232 with a distally positioned device member 234 which is shown in a closed configuration in FIG. 13 and in an open and drug released configuration in FIG. 14. The device member 234 has a hollow chamber inside for storing a desired drug for delivery to a location within a body cavity such as a blood vessel. Alternatively, the device member 234 can store and delivery other medical devices suitably sized so that they can be carried within device member 234. The drug within device member 234 can be discharged by saline fluid which can be injected into the device member 234 through a suitably provided lumen within catheter shaft 232. Alternatively mechanical release systems can also be employed.

Yet additional alternative embodiments of the present invention are shown in FIGS. 15 through 21. In these embodiments, the guidewire channel which is attached to the body member starts distal to the balloon and terminates at a point which is just proximal to the balloon and this channel is actually a plurality of sleeves which are underlying the balloon with a gap between them.

The guidewire channel, which can be a plurality of sleeve members generally within the balloon, is non cylindrical and has a diameter at the distal tip of the balloon lower than at the proximal tip which is higher. Therefore, the diameter generally increases toward the proximal end of the catheter. However, such increase in diameter is not necessarily constantly increasing, however but may vary toward the non-proximal end. Therefore, for some lengths the diameter may be increasing, then constant, then increasing again and the like. Alternatively, the diameter can increase constantly toward the proximal end. Generally, the diameter may be of a non uniform cross-section. Other structural variations include: the length of the sleeve, the gap between the sleeves, the diameter to length ratio between the sleeves, and the diameter of the sleeve.

By way of example, the guidewire lumen generally in the middle of the balloon is not a straight (cylindrical) lumen but it is more pointed in the distal end and increases in diameter until the point at which the guidewire exits at the first exit point. The guidewire lumen passes through the balloon and terminates at a point proximal to the balloon. This lumen is actually a plurality of sleeves that are underlying within the balloon segment. This guidewire segment described above can have only two sleeves under the balloon and one of the sleeves can form a substantial length of the balloon and the other sleeve can be of a smaller length inside the balloon. There is a gap between the sleeves inside the balloon and this provides at least one differentiation of the present invention from prior devices, whereby the guidewire member is not an integral cylindrical tube attached to the body member but actually has a gap which is inside the balloon.

The sleeves upon termination outside the balloon can extend all the way throughout the length of the body member or can terminate proximal to the balloon. If desired, the sleeves can extend up to ¼ distance of the body member or less than ½ the distance. Alternatively, the sleeves can extend up to ½ the distance of the body member or less than ½ the distance. In another embodiment, the sleeves can extend up to ¾ the distance of the body member or less than ¾ the distance. Also, the sleeves can extend up to the full distance of the body member. When the sleeves extend beyond ½ the distance of the body member, then a hypotube shaft is not needed at the proximal end of the body member, since the extension of the sleeves can provide the support that the catheter requires.

The plurality of sleeves are also preferably increasing in diameter. The farther the sleeves extend the greater their diameter. The first sleeve can be of a diameter x, the second sleeve can have a slightly increasing diameter, and the third sleeve can be of slightly increasing diameter than that of the second sleeve. Preferably, the sleeve that is passing inside the balloon is of increasing diameter only. The other sleeves which form the plurality can be of constant diameter. The sleeve inside the balloon is preferably of a slightly increasing diameter. While the distal tip of the catheter could have an internal diameter of 0.015", the end of the first sleeve proximal to the balloon could have an internal diameter of 0.016" or even up to 0.017".

The plurality of sleeves could also be of decreasing diameter, where the plurality of sleeves decrease in diameter as the number of sleeves increase.

The gap between the sleeves can be uniform or generally non uniform. For example, the gap between the first sleeve and the second sleeve can be 3 centimeters ("cm"), the gap between the second sleeve and the third sleeve can be 4 cm, the gap between the third sleeve and the fourth sleeve can be 3 cm and so on. The uniformity or the non uniformity can extend along the length of the sleeve members.

The length of the sleeves can also vary. In the embodiment wherein the sleeves extend inside the balloon, the first sleeve may be at least 1.5 times the length of the balloon and this could be as much as two to three times. The remainder of the sleeves are less than or equal to the length of the balloon. No direct or indirect correlation is intended between the length of the balloon and the length of the sleeves, this is given for exemplary comparative purposes only.

While the guidewire lumen as defined in known devices is essentially cylindrical in shape to accommodate a guidewire which is usually of lumen 0.014" in diameter, the guidewire lumen according to the present invention may be of increasing diameter or conical in shape. This shape of the cone is on the body member where the sleeve member terminates. Only the lumen is intended to be a cone and the outside segment does not have a cone. Any shape other than a cylinder is recommended for this function, and one of ordinary skill in the art can select the optimum shape for the particular design and the intended function in accordance with the teachings herein.

The sleeve members with the gaps generally provide the following functionality. There is friction between the guidewire channel or the sleeve members and the guidewire essentially and this has to be overcome and the catheter pushed with a force that exceeds the friction plus the pushing force. The plurality of the sleeve members also acts like the wheels on a rail and provide the backbone which gives it the trackability. This trackability exceeds the trackability of the currently existing catheters. The pushability of the catheter is much better when compared to known catheters because the guidewire is intermittently exposed on the guidewire channel. The flexibility of the distal segment of the catheter is far better and the sleeves allow for small radius of turning during curves in the arteries. The inside of the sleeve members can be coated with lubricious material to ensure that the guidewire is extremely slippery when passed through it.

Because the sleeve member inside the balloon segment is conical in shape, it allows for a smoother transition zone at the ends of the balloon. Also, the proximal most sleeve member on the catheter body which is farthest from the balloon provides for a smooth transition segment with the body of the catheter.

In the embodiment where there is no plurality of sleeve members and just one sleeve running midway or otherwise into the balloon, this sleeve member is conically shaped such that the diameter of the distal outlet is smaller than the diameter of the proximate outlet.

The catheter can sometimes be reinforced with a hypotube or a wire inside the body member to enable it to be more pushable. Because of the sleeves and also the gaps between them, it may not be necessary to have such a hypotube or stiffening wire as the external guidewire provides all the pushability.

In FIG. 15, there is schematically shown a catheter 300 wherein the guidewire lumen is formed of sleeve member 302 through balloon 304 and also includes four sleeve members 306, 308, 309, and 310 outside the balloon. Preferably the sleeve member 302 has a non-uniform cross section. In a preferred embodiment, sleeve member 302 is conical, truncated or tapered, i.e., it has an increasing cross sectional diameter from the distal end portion to the proximal end portion. As shown in FIGS. 16A and 16B, the cross-section in the direction A—A at the distal end is smaller than at the proximal end in the direction B—B.

Referring to FIG. 17, the catheter 312 has a guidewire channel 314 which is parallel to the body member inside the balloon. The sleeve members 316 and 318 outside the balloon are of varying length. They are also spaced equidistantly.

In FIG. 18, the catheter 320 has a guidewire channel that is parallel to the body member of the catheter and is formed of three sleeve members 322, 324, and 326. These sleeve members can be of the same or varying sizes and spaced apart at different or equal distances. Preferably, the sleeve members can be conical so that the cross section increases from 322 to 324 and again to 326. Also, preferably, the cross section can increase continuously and progressively along the lengths of these sleeve members.

Figure 19:
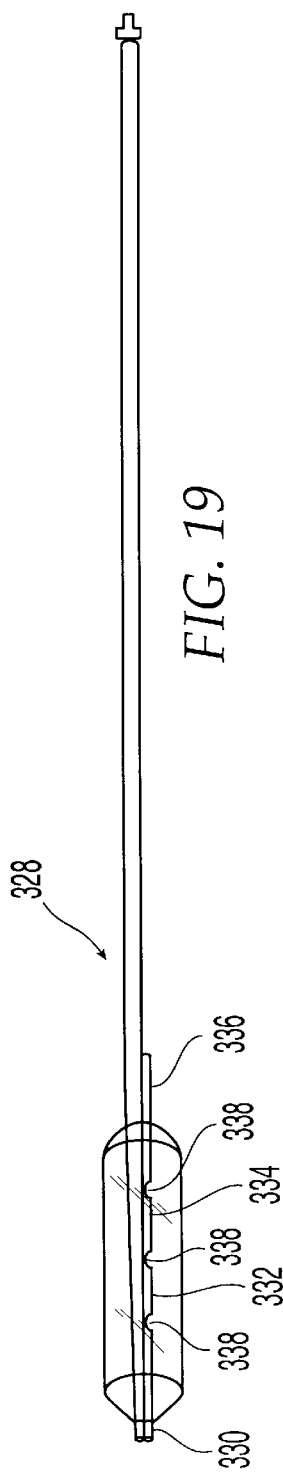
FIG. 19 is a side view of yet another embodiment of a balloon catheter according to the present invention wherein the guidewire channel is a long sleeve with slits under the balloon.

Turning now to FIG. 19, the catheter 328 has a guidewire channel is formed of four sleeve members 330, 332, 334, and 336 which are formed by slots or cutouts 338. Here again, the sleeve members can be of varying lengths and preferably can be conical in shape.

Figure 20:
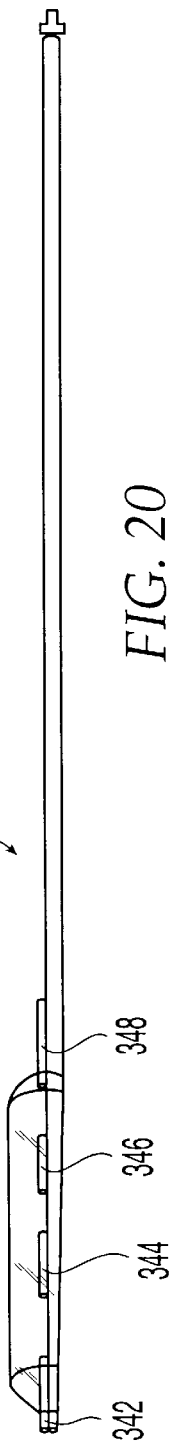
FIG. 20 is a side view of still another embodiment of a balloon catheter according to the present invention wherein the guidewire channel includes four sleeve members.

In FIG. 20, the catheter 340 includes four sleeve members 342, 344, 346, and 348 through the balloon to form the guidewire channel. The sleeve members are spaced apart at equal or different distances along the and can be conical in shape.

Figure 21:
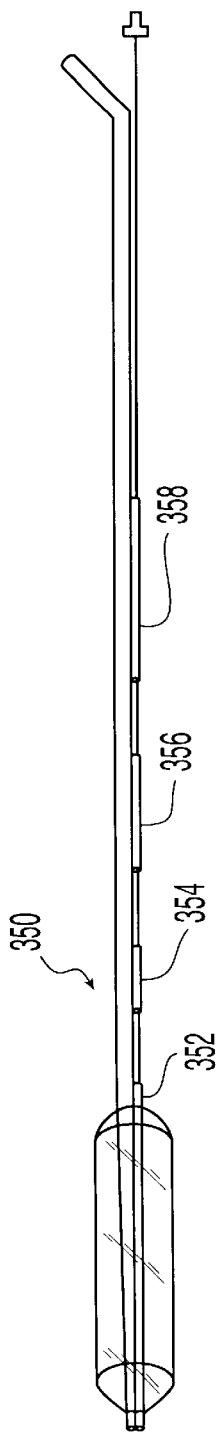
FIG. 21 is a side view of another embodiment of a balloon catheter according to the present invention wherein there is a single sleeve through the balloon and three sleeve members disposed outside of the balloon.

In FIG. 21, the catheter 350 includes four sleeve members 352, 354, 356, and 358, with the first sleeve member 352 being positioned under the balloon and the remaining three guide members 354, 356, and 358 being spaced along the through body member. Guide members 354, 356, and 358, as shown, are of increasing length to assist in guiding the guide wire to the distal end of the catheter. If desired, the guide members 354, 356, and 358 can be of essentially the same length, although the increasing length design that is shown is advantageous in that shorter and shorter lengths of guide members eliminate unnecessary material. The guide members may be conical in shape, if desired.

Figure 22:
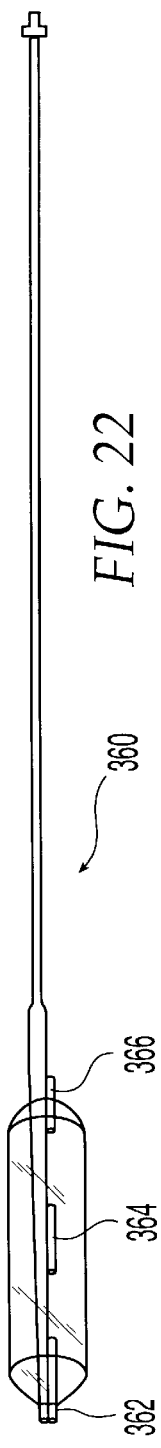
FIG. 22 is a side view of another embodiment of a balloon catheter according to the present invention wherein the guidewire lumen through the catheter is formed of three sleeve members which are integral with the lumen extending along the length of the catheter.

In FIG. 22, the catheter 360 includes three sleeve members 362, 364, and 366 positioned beneath the balloon to form the guidewire channel. These sleeve members may be essentially equal in length and are preferably spaced apart equidistantly beneath the balloon. If desired, the sleeve members 362, 364, and 366 may have increasing lengths similar to those of FIG. 21, they may be arranged in other than equidistant spacing and may be conical in shape.

Figure 23:
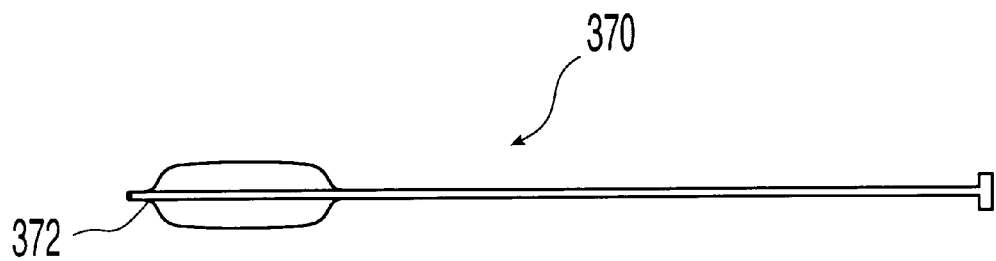
FIG. 23 is a side view of another embodiment of a balloon catheter according to the present invention wherein there is a double lumen through the balloon and a single lumen outside of the balloon and the guidewire lumen through the balloon is conical in shape, i.e., it has a larger diameter at its proximal end than at its distal end and has an increasing diameter from the distal end to the proximal end.

In FIG. 23, the catheter 370 includes a guidewire channel that is integrated within the balloon and has only one sleeve member 372 extending from the distal tip of the balloon to the proximal tip of the balloon.

Figure 24:
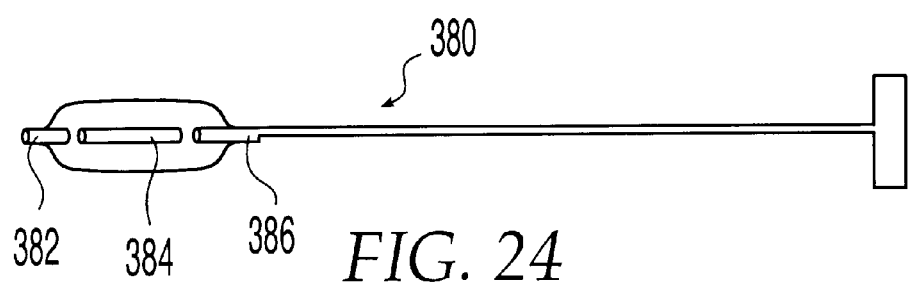
FIG. 24 is a side view of another embodiment of a balloon catheter according to the present invention wherein there is a single conical (or tapering) guidewire lumen through the balloon and which guidewire lumen has multiple sleeve members or sections inside the balloon.

FIG. 24 shows an alternative embodiment of that shown in FIG. 23 with the catheter 380 having a guidewire channel that is integrated within the balloon and has a plurality of spaced sleeve members 382, 384, and 386 extending from the distal tip of the balloon to the proximal tip of the balloon. The sleeve members do not extend substantially all the way on the body member but extend just proximal to the balloon. As above, these sleeve members may have different lengths or may be essentially equal in length and are preferably spaced apart equidistantly beneath the balloon. If desired, the sleeve members 382, 384, and 386 may be arranged in other than equidistant spacing and may be conical in shape.

Figure 25:
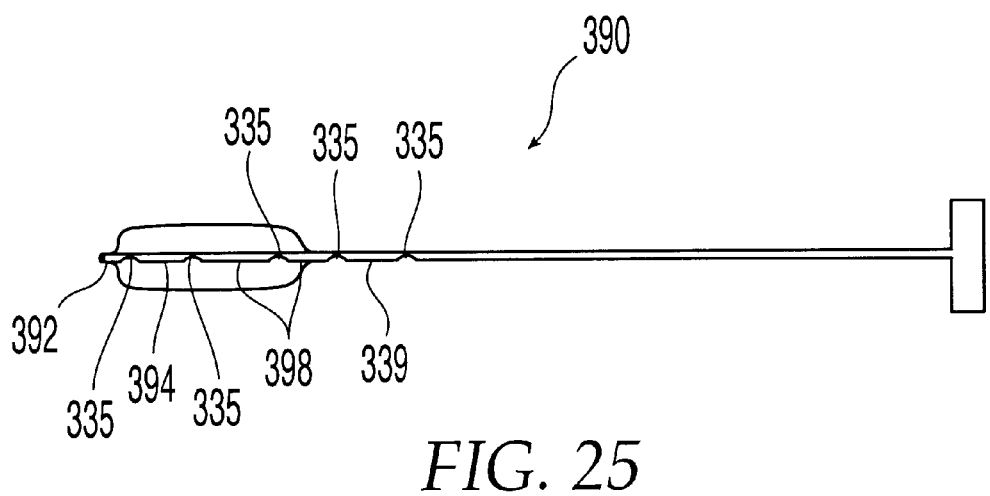
FIG. 25 is a side view of another embodiment of a balloon catheter according to the present invention wherein there is a single conical (or tapering) guidewire lumen through the balloon and which guidewire lumen has slits that form a non continuous channel under the balloon.

Another variation is shown in FIG. 25, where the catheter 390 has a guidewire channel which is formed of four sleeve members 392, 394, 336, 338, and 339 which are formed by slots or cutouts 335. Here again, the sleeve members can be of equal or varying lengths and are preferably spaced apart equidistantly beneath the balloon. If desired, the sleeve members may be arranged in other than equidistant spacing and may be conical in shape.

With respect to the embodiments described and illustrated herein wherein there is only one lumen within the balloon, any gaps or openings between the sleeves will not inflate the balloon because of leakage through the gaps. In such case, an external sheath or bridge may be placed between the sleeves and thus slightly overlap the two sleeves such that the bridge is permanently fixed between the two sleeves. The balloon can then be mounted on the two sleeves. This arrangement will provide that the guidewire does not kink when passing through a bend, and also this bridge serves the purpose of not letting any dye or air leak when the balloon is being inflated. While the two sleeves themselves can be made of coils, wires or polymer, the bridge is made of a plastic material preferably a heat shrinkable polymer which has an ultra thin wall thickness. This bridge can also be made of a radiopaque material so that the entire section can be visualized under fluoroscopy.

Figure 26:
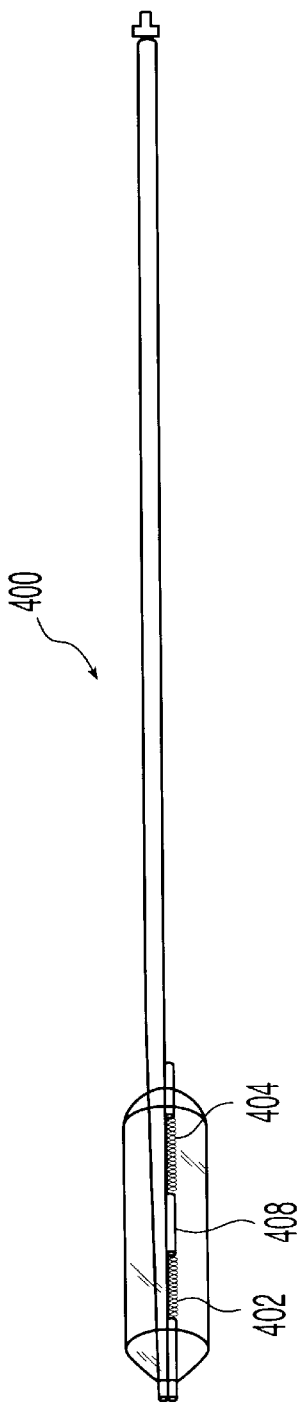
FIG. 26 is a side view of another embodiment of a balloon catheter according to the present invention wherein two sleeve members are made of a coil and a bridging member spans the gap between the sleeve members.

FIG. 26 shows the distal portion of a catheter 400 having two sleeve members 402, 404 that span the length of a balloon 406. Each of sleeve members 402, 404 is made of a coil or wire. The coil or wire provides flexibility. A bridging member 408 spans the gap between sleeve members 402, 404 to prevent the fluid (liquid or gas) used to dilate balloon 406 from escaping through the gap and out sleeve members 402, 404. Bridging member 408 can be secured to sleeve members 402, 404 in a number of different ways, such as gluing, welding, or any similar fashion that will provide a fluid-tight seal. Bridging member 408 also provides flexibility and cross-ability to catheter 400 and can be used even if sleeve members are not coils or wires.

Figure 27:
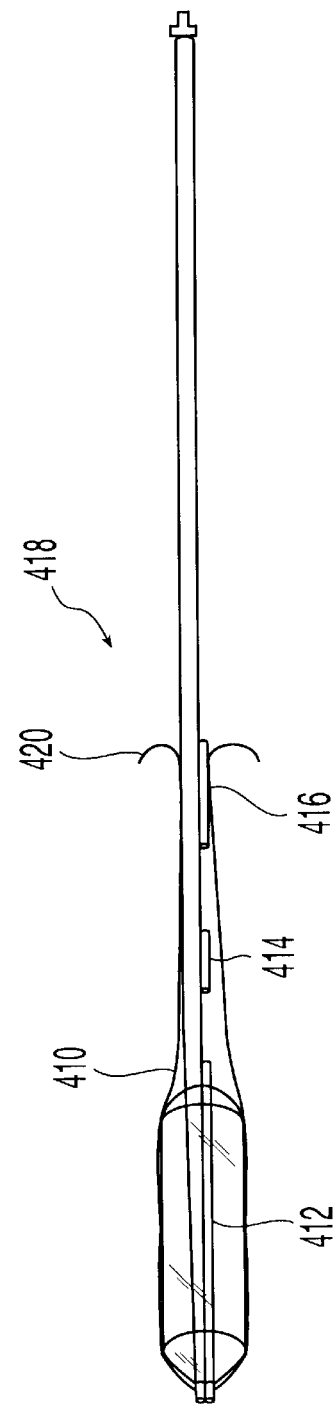
FIG. 27 is a side view of another embodiment of a balloon catheter according to the present invention wherein a peelable sheath covers the distal end of the catheter to facilitate insertion of a guidewire through the sleeve members.

In order to facilitate the insertion of the guidewire into the sleeve members, a peelable sheath can be provided to cover the balloon and sleeve members. As shown in FIG. 27, a peelable sheath 410 covers sleeve members 412, 414, 416. Sheath 410 serves as a temporary mechanism to allow a guidewire to be more easily passed through the entry and exit points of each of sleeve members 412, 414, 416. Sheath 410 is tightly secured to catheter 418 and extends from the entry point of the first sleeve member, sleeve member 412, to the exit point of the last sleeve member, sleeve member 416. With sheath 410 covering all of the sleeve members, the guidewire need just be inserted through the entry point of the first sleeve member and out the exit point of the last sleeve member, rather than having to thread the guidewire through the entry and exit points for each of the sleeve members. Once the guidewire is inserted into the sleeve members, sheath 410 can be peeled off and catheter 418 is ready to be moved on top of the guidewire and inside the patient's body. Sheath 410 can have a tab 420 to facilitate peeling.

While the present invention has been described and illustrated herein with respect to the preferred embodiments thereof, it should be apparent that various modifications, adaptations and variations may be made utilizing the teachings of the present disclosure. For example, the balloon may have only a single guidewire lumen beneath it where the catheter body has a dual lumen construction under the balloon and a single lumen construction for the remainder. As above, the guidewire lumen can have a plurality of spaced sleeve members extending from the distal tip of the balloon to the proximal tip of the balloon. In this arrangement, the sleeve members do not extend substantially all the way on the body member but extend just proximal to the balloon. Also as above, these sleeve members may have different lengths or may be essentially equal in length and are preferably spaced apart equidistantly beneath the balloon. If desired, the sleeve members may be arranged in other than equidistant spacing and may be conical in shape. It is intended that all these modifications are included within the scope of the claims without departing from the teachings of the present invention.

I claim:
1. A catheter comprising:
   a. a body member having a lumen;
   b. a balloon member disposed on the body member and communicating with the lumen;
   c. a plurality of sleeve members disposed on the body member along a length of the body member, each sleeve member having a passageway and the sleeve members with gaps between them extending a substantial length of the body member, wherein at least one sleeve member extends through the balloon member; and
   d. a sheath covering the plurality of sleeve members.

2. The catheter of claim 1 wherein at least one of the sleeve members is disposed adjacent the balloon member.

3. The catheter of claim 2 wherein the balloon adjacent sleeve members have a generally non uniform cross-section.

4. The catheter of claim 3 wherein at least one of the balloon adjacent sleeve members is generally conical and has a cross-section generally increasing in the proximal direction.

5. The catheter of claim 1 wherein at least one of the sleeve members is disposed in a distal region of the body member.

6. The catheter of claim 5 wherein the at least one of the sleeve members is disposed adjacent the balloon member and has a length greater than that of the balloon member.

7. The catheter of claim 5 wherein the at least one of the sleeve members is disposed generally centrally of the balloon member.

8. The catheter of claim 5 wherein the at least one of the sleeve members is disposed generally eccentrically of the balloon member.

9. The catheter of claim 1 wherein the body member has a plurality of apertures on the body member.

10. The catheter of claim 1 further comprising a guidewire dimensioned and configured for passing through the passageways of the sleeve members.

11. The catheter of claim 1 wherein the balloon has a coating containing a pharmacological agent.

12. The catheter of claim 1 wherein at least a portion of the catheter has a plurality of radiopaque markers.

13. An angioplasty catheter comprising:
   a. an elongated body member having a lumen which includes an opening adjacent its distal end and at least one opening adjacent its proximal end;
   b. a balloon member sealingly disposed on the elongated member adjacent its distal end, the elongated member having at least one opening communicating with the interior of the balloon and the lumen within the elongated body member;
   c. a plurality of sleeve members disposed on the elongated member, each sleeve member having a passageway and the sleeve members with gaps between them extending a substantial length of the body member, wherein at least one sleeve member extends through the balloon member; and
   d. a sheath covering the plurality of sleeve members.

14. The catheter of claim 13 wherein at least one of the sleeve members is disposed adjacent the balloon member.

15. The catheter of claim 14 wherein the balloon adjacent sleeve members have a generally non uniform cross-section.

16. The catheter of claim 15 wherein at least one of the balloon adjacent sleeve members is generally conical and has a cross-section generally increasing in the proximal direction.

17. The catheter of claim 13 wherein at least one of the sleeve members is disposed in a distal region of the body member.

18. The catheter of claim 17 wherein the at least one of the sleeve members is disposed adjacent the balloon member and has a length greater than that of the balloon member.

19. The catheter of claim 17 wherein the at least one of the sleeve members is disposed generally centrally of the balloon member.

20. The catheter of claim 17 wherein the at least one of the sleeve members is disposed generally eccentrically of the balloon member.

21. The catheter of claim 13 wherein the body member has a plurality of apertures on the body member.

22. The catheter of claim 13 further comprising a guidewire dimensioned and configured for passing through the passageways of the sleeve members.

23. The catheter of claim 13 wherein the balloon has a coating containing a pharmacological agent.

24. The catheter of claim 13 wherein at least a portion of the catheter has a plurality of radiopaque markers.

25. A catheter comprising:
  a. a body member having a lumen;
  b. a device member disposed on the body member;
  c. a plurality of sleeve members disposed on the body member, each sleeve member having a passageway therethrough; and
  d. a peelable sheath covering the plurality of sleeve members.

26. The catheter of claim 25 wherein the device member is a balloon member, a stent, or a container having a chamber.

27. The catheter of claim 25 wherein at least one of the sleeve members has a generally non uniform cross-section.

28. The catheter of claim 27 wherein the at least one of the sleeve members is generally conical and has a cross-section generally increasing in the proximal direction.

29. A method of using a catheter comprising:
  1. providing a catheter comprising:
    a. a body member having a lumen;
    b. a balloon member disposed on the body member and communicating with the lumen;
    c. a plurality of sleeve members disposed on the body member along a length of the body member, each sleeve member having a passageway and the sleeve members with gaps between them extending a substantial length of the body member, wherein at least one sleeve member extends through the balloon member; and
    d. a peelable sheath covering the plurality of sleeve members;
  2. selectively passing a guidewire through the passageways of the sleeve members, at least a portion of the guidewire being disposed in a body cavity;
  3. peeling the sheath from the catheter;
  4. inserting the catheter into the body cavity along the guidewire; and
  3. selectively inflating the balloon.

* * * * *